United States Patent [19]

Ohno et al.

[11] 4,245,116

[45] Jan. 13, 1981

[54] RACEMIZATION OF OPTICALLY ACTIVE 2-(4-CHLOROPHENYL)-3-METHYL-BUTYRIC ACID

[75] Inventors: Nobuo Ohno, Toyonaka; Masakazu Miyakado; Hajime Hirai, both of Nishinomiya, all of Japan

[73] Assignee: Sumitomo Chemical Company, Limited, Osaka, Japan

[21] Appl. No.: 967,948

[22] Filed: Dec. 11, 1978

Related U.S. Application Data

[63] Continuation of Ser. No. 811,926, Jun. 30, 1977, abandoned.

[30] Foreign Application Priority Data

Jun. 30, 1976 [JP] Japan .................................. 51-78089

[51] Int. Cl.³ ............................................. C07B 20/00
[52] U.S. Cl. ..................................... 562/401; 562/496
[58] Field of Search .............................. 562/401, 496

[56] References Cited

U.S. PATENT DOCUMENTS

| | | | |
|---|---|---|---|
| 2,859,244 | 11/1958 | White | 562/401 |
| 3,213,106 | 10/1965 | Sasaji et al. | 562/401 |
| 3,686,183 | 8/1972 | Dyson | 562/401 |

*Primary Examiner*—Natalie Trousof
*Assistant Examiner*—Vera C. Clarke
*Attorney, Agent, or Firm*—Sughrue, Rothwell, Mion, Zinn and Macpeak

[57] ABSTRACT

A method for racemization of optically active 2-(4-chlorophenyl)-3-methylbutyric acid which comprises the steps of (a) reacting optically active 2-(4-chlorophenyl)-3-methylbutyric acid with a hydroxide or carbonate of an alkali metal or alkaline earth metal at a temperature of more than 110° C. to produce a racemate of the alkali metal or alkaline earth metal salt of the above acid, and (b) converting the resulting racemate of the salt to the acid.

9 Claims, 1 Drawing Figure

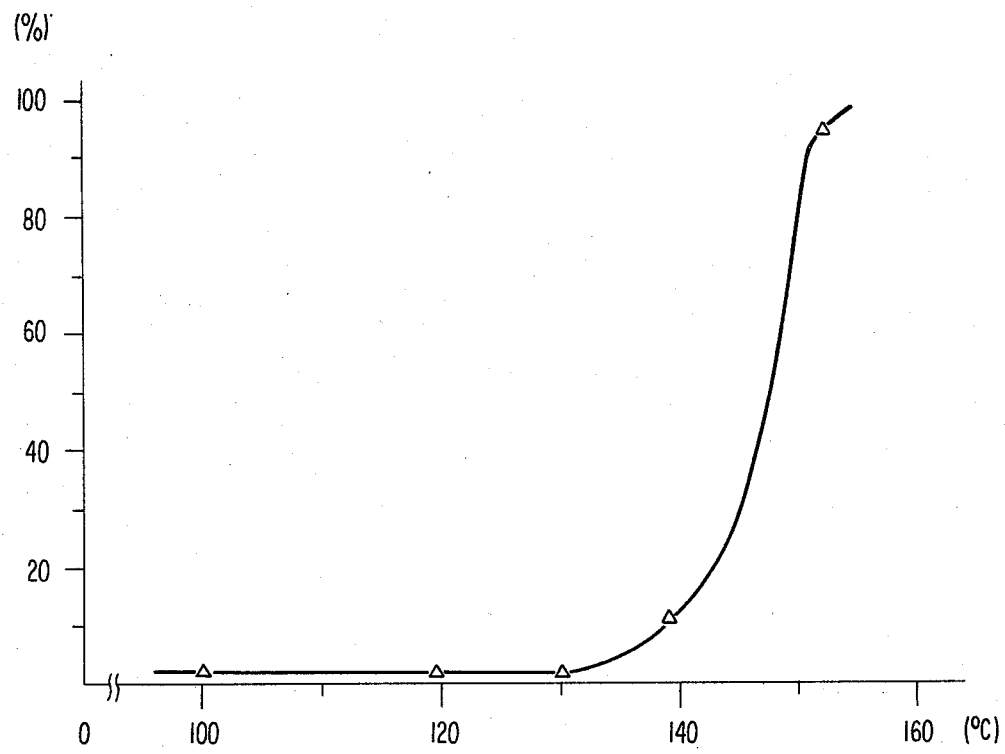

RACEMIZATION OF OPTICALLY ACTIVE 2-(4-CHLOROPHENYL)-3-METHYLBUTYRIC ACID

This is a continuation of application Ser. No. 811,926, filed June 30, 1977 now abandoned.

BACKGROUND OF THE INVENTION

The present invention relates to a method for racemization of optically active 2-(4-chlorophenyl)-3-methylbutyric acid which is an important intermediate for synthesizing a group of α-substituted phenylacetic esters having an insecticidal activity.

The inventors previously have found a group of α-substituted phenylacetic esters which are very different in chemical structure from conventional insecticides but have a strong insecticidal and miticidal activities on various kinds of harmful insects, as disclosed in U.S. Pat. Nos. 3,996,244 and 4,016,179 and U.S. patent application Ser. Nos. 557,694 (filed Mar. 12, 1975), now U.S. Pat. Nos. 4,058,622, 596,332 (filed July 16, 1975), 596,333 (filed July 16, 1975), now U.S. Pat. Nos. 4,016,179, 596,334 (filed July 16, 1975), now U.S. Pat. Nos. 4,062,968, 596,335 (filed July 16, 1975), now U.S. Pat. Nos. 4,039,680, and 596,336 (filed July 16, 1975), now U.S. Pat. No. 4,031,235.

The inventors have resolved the α-substituted phenylacetic acid which is the acid moiety of the esters into the optically active (+)-carboxylic acid isomer and (−)-carboxylic acid isomer, and examined the insecticidal and miticidal activities of the esters of each isomer. As a result, they have found that the esters of the (−)-carboxylic acid isomer have little or no practical activity, while those of the (+)-carboxylic acid isomer exhibit activity about two times as great as that of the racemate. The process developed by the inventors for optical resolution of this series of α-substituted phenylacetic acids is described in Japanese Patent Application (OPI) Nos. 25,544/1975 and 106,935/1975.

The inventors also studied a method for racemization of the (−)-carboxylic acid isomer obtained as a result of the optical resolution described above, for the purpose of finding an effective use for the (−)-isomer.

DESCRIPTION OF THE PRIOR ART

Racemization of optically active α-substituted phenylacetic acid derivatives has not been extensively studied. Exemplary of the prior work are the following reports on racemization:

A. Horeau et al. reported that optically active α-ethylphenylacetic acid chloride was easily racemized in pyridine (0.4 M solution) at room temperature and that the rate of racemization was such that the optical rotation decreased to one-seventh of its initial value in about 3 hours (Bull soc. chim. Fr., 1967, 117). In the same report Horeau et al describe that optically active α-ethylphenylacetic anhydride was racemized in pyridine at room temperature. The rate of racemization was such that the optical rotation decreased to one-half of the initial value in as long as 20 hours when the concentration of the pyridine solution was 0.1 M, while the racemization completely came to an end in about 8 hours when the concentration was 0.6 M.

B. Ph. Gold-Aubert reported that optically active N-α-(α-ethylphenylacetyl)urea was racemized by about 73% when heated under reflux for 90 minutes in 0.5 N NaOH in 50% aqueous ethanol (Helv. Chem. Acta., 168, 1513 (1958)).

C. R. S. Stuart et al. examined the rate at which the hydrogen atom in the α-position of phenylacetic acids was exchanged when the sodium salt of the acids was heated in deuterium oxide containing an alkali. They reported that the rate of exchange relative to the rate for sodium phenylacetate was about 1/270 for sodium α-methylphenylacetate and only about 1/42,000 for sodium α-isopropylphenylacetate (J. Chem. Soc., Chem. Commun. 1969, 1068).

Optically active 2-(4-chlorophenyl)-3-methylbutyric acid (i.e., α-isopropyl-4-chlorophenylacetic acid), the compound with which the present invention is concerned, is an unknown compound in the literature; therefore, no information on the racemization of this compound appears in the literature.

BRIEF DESCRIPTION OF THE DRAWING

The FIGURE shows graphically the rate of conversion (ordinate) of the optically active acid in a 2.5% aqueous sodium hydroxide to the racemate as a function of temperature (abscissa). The results presented in the graph are those of Example 4 hereinafter.

DESCRIPTION OF THE INVENTION

As a result of preliminary tests, the inventors found that the racemization of optically active 2-(4-chlorophenyl)-3-methylbutyric acid does not proceed substantially by merely heating an aqueous solution of the sodium salt of the compound at about 100° C. in the usual manner. As set forth in Reference Example 1, racemization under these conditions were tried for 6 hours but was not observed. Another method attempted involved conversion of this compound to an organic tertiary amine salt followed by attempted racemization in an organic tertiary amine at high temperatures. As shown in Reference Example 2 racemization was not observed by this procedure either. It was concluded therefore that the racemization of this compound is very difficult by the procedures suggested by the prior art. It may be considered the possibility of racemization of optically active carboxylic acids will increase by first converting the acids to easily racemizable derivatives such as the acid chloride and acid anhydride. However, in order to use the resulting racemates in optical resolution again, it is most desirable to racemize the acid itself or metallic salts thereof. For this reason, the inventors extensively studied racemization of optically active α-isopropyl-4-chlorophenylacetic acid in the form of its alkali metal salts or alkaline earth metal salts. For example, the inventors attempted racemization in a 2.5% aqueous sodium hydroxide solution; racemization did not proceed at all, as shown in the Figure, until the temperature reached about 130° C. However, when the temperature reached about 130° C., racemization was observed unexpectedly, and thereafter the rate of racemization increased rapidly with increases in the reaction temperature: the rate of conversion exceeded 10% after 5 hours at 140° C. That is to say, the inventors found that using a high temperature of more than about 130° C. racemization of the compound 2-isopropyl-4-chlorophenylacetic acid can be achieved in a dilute aqueous alkali solution. This is very unexpected in view of conventional data.

Next, the inventors extensively studied decrease of the reaction temperature; They found that the temperature can be decreased to about 110° C. by increasing the concentration of aqueous alkali solution. For example, the rate of conversion was about 7% after 5 hours at 110° C. when 50% aqueous potassium hydroxide solution was used. Consequently, the racemization in accordance with this invention may be carried out at any temperature of more than 110° C., usually from 110° to 300° C., but the range of 120° to 200° C. is preferable from an industrial point of view. When the concentration of the aqueous alkali solution is low, the use of pressure reactors such as an autoclave is necessary to reach the required temperatures. When the alkali concentration is high, the required temperature can easily be reached by merely heating at atmospheric pressure. Reaction solvents are not necessarily essential to the racemization, but the use of solvent is desirable in order to permit the reaction to proceed smoothly. Examples of useable solvents include water, alcohols (e.g. methanol, ethanol, butanol, octanol), glycols (e.g. ethylene glycol, diethylene glycol, propylene glycol), mono or di-lower alkyl ether of glycols (e.g. ethylene glycol monomethyl ether, ethylene glycol monobutyl ether, ethylene glycol diethyl ether), glycerin and the like. As the hydroxides of alkali metal or alkaline earth metal or as the carbonates of alkali metal or alkaline earth metal useful in practicing this invention, there may be exemplified sodium hydroxide, potassium hydroxide, lithium hydroxide, barium hydroxide, calcium hydroxide, sodium carbonate, potassium carbonate and the like. The present invention is not, however, limited to these compounds.

It is necessary that the hydroxide or carbonate is used in more than equimolar amount with the carboxylic acid; from about 1.1 to 30 time by mole is desirable from an industrial point of view.

Next, the present invention will be illustrated in more detail with reference to the following examples and reference examples; The present invention is not, of course, limited to these examples.

EXAMPLE 1

A mixture of 2.13 g of (−)-isomer rich α-isopropyl-4-chlorophenylacetic acid ($[\alpha]_D^{22.5}$ −44.5°) and 15 g of 50% aqueous potassium hydroxide solution was refluxed with heating for 5 hours (the temperature of the reaction solution 136° C.). After cooling the mixture to room temperature, the deposited crystal was dissolved in 20 ml of cold water and the resulting solution was acidified to a pH of 1 with concentrated hydrochloric acid. The deposited carboxylic acid was extracted with benzene and the benzene was removed by evaporation from the separated organic layer. After drying, 2.11 g of racemized α-isopropyl-4-chlorophenylacetic acid was obtained. The rate of conversion was about 98%. $[\alpha]_D^{23.0}$ −0.72°. The rate of conversion was calculated in accordance with the equation:

$$\left(1 - \frac{[\alpha]_D^{after\ reaction}}{[\alpha]_D^{before\ reaction}}\right) \times 100\ (\%)$$

EXAMPLE 2

The procedure of Example 1 was repeated at reaction temperatures of 100° C., 110° C., 120° C. and 150° C. The rates of conversion at these temperatures after 5 hours were 0%, 10.5%, 21.4% and 98.4%, respectively.

EXAMPLE 3

4.80 g of (−)-isomer rich α-isopropyl-4-chlorophenylacetic acid ($[\alpha]_D^{23}$ −42.20°) was dissolved in 54 g of 2.5% aqueous sodium hydroxide solution. The resulting solution was placed in an autoclave and kept at 150° C. for 5 hours with stirring. After cooling to room temperature, the reaction solution was acidified to a pH of 1 with concentrated hydrochloric acid. The deposited carboxylic acid was extracted with benzene and the benzene was removed by evaporation from the separated layer. After drying, 4.74 g of the racemized, carboxylic acid was obtained. The rate of conversion was about 94%.
$[\alpha]_D^{24.0}$ −2.41°.

EXAMPLE 4

The procedure of Example 3 was repeated at reaction temperatures of 120° C., 130° C., 140° C. and 150° C. The results are shown in the Figure.

EXAMPLE 5

5.30 g of (−)-isomer rich α-isopropyl-4-chlorophenylacetic acid ($[\alpha]_D^{24}$ −46.56°) was mixed with 2.10 g of potassium hydroxide and 50 ml of ethylene glycol, and the resulting mixture was kept at 170° C. for 15 hours. The reaction solution was cooled to room temperature, diluted with 250 ml of water and acidified to a pH of 1 with concentrated hydrochloric acid. Thereafter, the same procedure as in Example 1 was carried out to obtain 5.19 g of racemized α-isopropyl-4-chlorophenylacetic acid. The rate of conversion was about 95%.
$[\alpha]_D^{22.0}$ −2.07°.

EXAMPLE 6

9.60 g of (−)-isomer rich α-isopropyl-4-chlorophenylacetic acid ($[\alpha]_D^{22.5}$ −49.00°) was mixed with 20.8 g of sodium hydroxide, 29.2 g of potassium hydroxide and 50 ml of water. The resulting mixture was kept at 138° C. for 5 hours with stirring. After cooling to room temperature, the same procedure as in Example 1 was carried out to obtain 9.25 g of the racemized carboxylic acid. The rate of conversion was about 73%.
$[\alpha]_D^{23.0}$ −13.48°.

EXAMPLE 7

A mixture of 5.30 g of (−)-isomer rich α-isopropyl-4-chlorophenylacetic acid ($[\alpha]_D^{22}$ −27.40°) and 103.6 g of 10% aqueous potassium carbonate solution was placed in an autoclave and kept at 200° C. for 5 hours with stirring. After cooling to room temperature, the same procedure as in Example 1 was carried out to obtain 4.95 g of the racemized carboxylic acid. The rate of conversion was about 63%. $[\alpha]_D^{23.0}$ −10.06°.

REFERENCE EXAMPLE 1

5.30 g of (−)-isomer rich α-isopropyl-4-chlorophenylacetic acid ($[\alpha]_D^{24.0}$ −46.56°) was mixed with 1.15 g of sodium hydroxide and 50 ml of water. The resulting mixture was heated at 100° C. for 6 hours with stirring. After cooling to room temperature, the same procedure as in Example 1 was carried out to obtain 5.22 g of the carboxylic acid. Substantially no conversion was obtained. $[\alpha]_D^{22.0}$ −46.17°.

REFERENCE EXAMPLE 2

4.00 g of (−)-isomer rich α-isopropyl-4-chlorophenylacetic acid ($[\alpha]_D^{22.5}$ −40.09°) was dissolved in 50 g of quinoline and the resulting solution was kept at 135° to 138° C. for 4 hours. After cooling to room temperature, the reaction solution was diluted with 200 g of ice water and extracted with two 50 ml portions of benzene. The aqueous layer was acidified to a pH of 1 with conc. hydrochloric acid, and the deposited crystals were extracted with benzene. The benzene was removed by evaporation from the separated organic layer and the residue was dried to obtain 3.75 g of the carboxylic acid. Substantially no conversion was obtained. $[\alpha]_D^{23.0}$ −40.79°.

While the invention has been described in detail and with reference to specific embodiments thereof, it will be apparent to one skilled in the art that various changes and modifications can be made therein without departing from the spirit and scope thereof.

What is claimed is:

1. A method for racemization of optically active 2-(4-chlorophenyl)-3-methylbutyric acid which comprises the steps of:
    (a) reacting said acid with a hydroxide or carbonate of an alkali metal or alkaline earth metal at a temperature of more than 110° C., wherein the amount of said hydroxide or carbonate is, on a molar basis, greater than the amount of said acid, to produce a racemate of the alkali metal or alkaline earth metal salt of said acid, and
    (b) converting said racemate of the salt of said acid to said acid.

2. The method of claim 1, wherein said alkali metal is sodium or potassium.

3. The method of claim 1, wherein the amount of said hydroxide or carbonate is between about 1.1 and 30 moles per mole of said acid.

4. The method of claim 1, wherein step (a) is performed in a solvent.

5. The method of claim 1, wherein step (a) is performed at a temperature between 110° and 300° C.

6. The method of claim 1, wherein said solvent is water.

7. The method of claim 5, wherein step (a) is performed at a temperature between 120° and 200° C.

8. The method of claim 1, wherein step (a) is performed by reacting said acid with an alkali metal hydroxide or carbonate.

9. The method of claim 1, wherein said optically active acid is (−)-isomer rich 2-(4-chlorophenyl)-3-methylbutyric acid.

* * * * *